US008249691B2

(12) United States Patent
Chase et al.

(10) Patent No.: US 8,249,691 B2
(45) Date of Patent: Aug. 21, 2012

(54) GLOBAL MOTION INVARIANT SIGNATURES FOR FAST AND ACCURATE MOTION TRACKING IN A DIGITAL IMAGE-BASED ELASTO-TOMOGRAPHY SYSTEM

(75) Inventors: James Geoffrey Chase, Christchurch (NZ); Christopher Eric Hann, Rangiora (NZ); Lawrence Allen Ray, Rochester, NY (US)

(73) Assignee: Boundary Life Sciences, Christchurch (NZ)

( * ) Notice: Subject to any disclaimer, the term of this patent is extended or adjusted under 35 U.S.C. 154(b) by 0 days.

(21) Appl. No.: 13/037,046

(22) Filed: Feb. 28, 2011

(65) Prior Publication Data
US 2011/0208043 A1    Aug. 25, 2011

Related U.S. Application Data

(62) Division of application No. 11/749,594, filed on May 16, 2007, now abandoned.

(51) Int. Cl.
*A61B 5/05* (2006.01)
(52) U.S. Cl. ........................................ 600/426; 382/128
(58) Field of Classification Search .................. 600/407, 600/425–428, 437–439, 476
See application file for complete search history.

(56) References Cited

U.S. PATENT DOCUMENTS

| | | | |
|---|---|---|---|
| 5,474,070 A | 12/1995 | Ophir et al. | |
| 5,524,636 A | 6/1996 | Sarvazyan et al. | |
| 5,810,731 A | 9/1998 | Sarvazyan et al. | |
| 6,270,459 B1 | 8/2001 | Konofagou et al. | |
| 6,494,834 B2 | 12/2002 | Konofagou et al. | |
| 6,514,204 B2 | 2/2003 | Alam et al. | |
| 6,585,647 B1 | 7/2003 | Winder | |
| 7,421,369 B2 * | 9/2008 | Clarkson | 702/150 |
| 2004/0015079 A1 | 1/2004 | Berger et al. | |
| 2004/0165767 A1 | 8/2004 | Gokturk et al. | |

FOREIGN PATENT DOCUMENTS
WO    WO 03/022152 A1    3/2003

OTHER PUBLICATIONS

Brown, R.G., Hann, C.E., Chase, J.G., Ray, L. (2007) Discrete Colour-based Euclidean-Invariant Signatures for Feature Tracking in a DIET Breast Cancer Screening System. San Diego, CA, USA: SPIE Medical Imaging Conference—Physiology, Function, and Structure from Medical Images, Feb. 17-22, 2007.*
Jan Modersitzki, Numerical Methods for Image Registration pp. 1-7, 27-74, 175-186 (Oxford University Press, New York, 2004).

(Continued)

*Primary Examiner* — Parikha Mehta
(74) *Attorney, Agent, or Firm* — Hiscock & Barclay, LLP

(57) ABSTRACT

A method for converting digital images of an actuated breast into an accurate description of breast surface motion from a digital image-based elasto-tomography system comprises the steps of artificially placing a high density of fiducial markers on the breast surface, whereby the fiducial markers have different qualities and are placed in different proportions according to their quality; utilizing motion invariant properties of the fiducial markers to form a global motion invariant signature; tracking the markers on the actuated breast surface from image to image in each digital camera using the global motion invariant signature; and using the cameras calibration to measure the breast surface motion.

21 Claims, 10 Drawing Sheets

OTHER PUBLICATIONS

J.P. Lewis, "Fast Normalized Cross-Correlation," (Vision Interface, 1995) [available online] [last retrieved on Dec. 12, 2007] Retrieved from the Internet <URL: http://www.idiom.com/~zilla/Work/nvisionInterface/nip.html>.

Michael Kass, Andrew Witkin & Demetri Terzopoulos, "Snakes: Active Contour Models," pp. 321-331, International Journal of Computer Vision (Kluwer Academic Publishers, Boston, 1998).

Natan Peterfreund, "Robust Tracking of Position and Velocity With Kalman Snakes," pp. 564-569, IEEE Transactions on Pattern Analysis and Machine Intelligence, vol. 21, No. 6 (Jun. 1999).

Qinfen Zheng & Rama Chellappa, "Automatic Feature Point Extraction and Tracking in Image Sequences for Arbitrary Camera Motion," pp. 31-76, 15 International Journal of Computer Vision (Kluwer Academic Publishers, Boston, 1995).

Haili Chui & Anand Rangarajan, "A New Point Matching Algorithm for Non-Rigid Registration," pp. 114-141, 89 Computer Vision and Image Understanding (2003).

Peters et al., Digital image-based elasto-tomography: first experiments in surface based mechanical property estimation of gelatine phantoms. JSME Int J. 48(4):562-569. 2005.

* cited by examiner

300 — Describe each red landmark point by the coordinate $(d_g, d_b)$, where $d_g$ and $d_b$ are the distances to the closest green and blue point respectively. The set of all points $(d_g, d_b)$ is the global signature for the red points.

302 — For each red point in the signature of the first image locate the closest red point in the signature of the second image. This provides an initial correspondence of red points between images.

304 — Choose the pairs of red points in the initial correspondence between images that differ by a distance less than a predetermined upper bound on motion. This will rule out a significant number of non-corresponding points.

306 — To rule out any further non-corresponding points that maybe left, for each remaining red point in the first image locate the first and second closest points to form a triangle. Compare the three distances on the edges of the triangle with the three distances of the corresponding triangle in the second image. If they are all within a tolerance accept the red point in the first image and corresponding red point in the second image, otherwise reject them both.

308 — The output is a set of corresponding red points between the first and second image which determines the motion field for the red points.

Figure 3

Blue dots in two images I (dots) and Ī (circles) related by a linear or affine transformation with random noise added Linear invariant signatures for the blue dots for image I (dots) and Ī (circles)

Registering the blue dots of image Ī (circles) onto the blue dots of image I (circles)

Randomly places circles of diameter 10 pixels

Non-uniform motion field

Using distances on edges of triangle to rule out the non-corresponding points denoted by circles An example of blue points in and Ī registered onto blue points of I Two 1 mega-pixel images of two different deformations of a visco-elastic breast phantom with randomly place coloured markings.

Registered blue points denoted by crosses

Motion field

GLOBAL MOTION INVARIANT SIGNATURES FOR FAST AND ACCURATE MOTION TRACKING IN A DIGITAL IMAGE-BASED ELASTO-TOMOGRAPHY SYSTEM

CROSS-REFERENCE TO RELATED APPLICATIONS

This application is a divisional of prior U.S. patent application Ser. No. 11/749,594, filed May 16, 2007, which is hereby incorporated by reference.

FIELD OF THE INVENTION

The invention relates generally to the field of breast cancer screening, and in particular to a technique of breast surface motion tracking in a digital image-based elasto-tomography system.

BACKGROUND OF THE INVENTION

Breast cancer is a significant health problem in both developed and developing countries. It is estimated that each year the disease is diagnosed in over 1,000,000 women worldwide and is the cause of death in over 400,000 women. There are many treatment options available, including surgery, chemotherapy, radiation therapy, and hormonal therapy. These treatments are significantly more effective in reducing the mortality of the disease with early detection through breast cancer screening programmes.

The standard method for detection of breast cancer is mammography. However mammography can cause significant patient discomfort and requires radiation exposure. Furthermore there are often variable results and inconsistencies in reading and interpreting the images of breast tissue from the X-Ray machine especially for smaller tumour sizes of the order of 1-5 mm.

Digital Image based Elasto-tomography is an emerging technology for non-invasive breast cancer screening without the requirement of radiation. As used herein, Digital Image-based Elasto-Tomography system will be referred to as a DIET system. The DIET system uses digital imaging of an actuated breast surface to determine tissue surface motion. It then reconstructs the three-dimensional internal tissue stiffness distribution from that motion. Regions of high stiffness suggest cancer since cancerous tissue is between 3 and 10 times stiffer than healthy tissue in the breast. This approach eliminates the need for X-Rays and excessive, potentially painful compression of the breast as required in a mammogram. Hence, screening could start much younger and enjoy greater compliance. Presently, there are other elasto-tomographic methods based on magnetic resonance and ultrasound modalities. Both methods are capable of measuring the tissue elasticity and they are undergoing rapid development across the globe. However, they are also costly, in terms of equipment, and take significant time to use. They are therefore limited for practical screening applications.

The DIET system, in contrast, is silicon based and is thus potentially low cost and portable, so the technology could be used in any medical centre, particularly in remote areas. In addition, the use of silicon technology ensures that as it improves and scales upward in capability so will the DIET system performance. This scalability of performance is not true for X-Ray or ultrasound based approaches.

The DIET system relies on a fast and accurate measurement of the actuated breast using multiple calibrated high-resolution digital cameras. Furthermore small perturbations and variations on the surface must be measured accurately to ensure smaller tumours are not missed. Therefore, there exists a need in the art for very high-resolution feature registration and motion tracking system that can deal with the unique requirements of a DIET system. In addition, for clinical effectiveness, the measured motion must be done with a minimal amount computation.

SUMMARY OF THE INVENTION

The present invention is directed towards overcoming the problem of very high resolution feature registration and motion tracking with a minimal amount of computation in connection with the DIET system; consisting of a patient bed, an actuator to induce oscillation in the breast, an array of digital cameras and computer software for processing images of the breast surface and transforming into measured motion, and computer software for converting measured motion into a three-dimensional distribution of stiffness of the breast.

Briefly summarized, according to one aspect of the invention a method for converting digital images of an actuated breast into an accurate description of breast surface motion from such a DIET system as described above comprises the steps of artificially placing a high density of fiducial markers on the breast surface, whereby the fiducial markers have different qualities and are placed in different proportions according to their quality; utilizing motion invariant properties of the fiducial markers to form a global motion invariant signature; tracking the markers on the actuated breast surface from image to image in each digital camera using the global motion invariant signature; and using the cameras calibration to measure the breast surface motion.

In one form, the invention is a method for generating a high resolution feature registration and motion tracking system with minimal computation wherein the method comprising the steps of artificially placing a plurality of fiducial markers on a surface of a breast, each of the markers having a characteristic according to a class of characteristics, the class having a plurality of subclasses wherein the markers in each subclass have a common characteristic, the subclasses each having a unique number of markers; tracking the motion of the markers of a first subclass having the fewest number of markers on the surface from a first image to a second image; partitioning the surface based upon the first subclass of markers; tracking the motion of the markers of a second subclass with the next fewest number of markers within each partition; and partitioning the surface based upon the second subclass of markers.

In another form, the invention is a method for generating a high resolution feature registration and motion tracking system with minimal computation in connection with a digital image-based elasto-tomography system, the method comprising the steps of: artificially placing a plurality of fiducial markers on a tissue surface; actuating the tissue surface; imaging the tissue surface with an array of digital cameras; choosing motion invariant properties of the fiducial markers to form a global motion invariant signature; tracking the markers on the actuated tissue surface from image to image in each digital camera using the global motion invariant signature; and using the tracked motion in each camera and the camera calibration to measure tissue surface motion.

In another form, the invention is a method for generating a high resolution feature registration and motion tracking system with minimal computation in connection with a digital image-based elasto-tomography system the method comprising the steps of: artificially placing a plurality of fiducial markers on a tissue surface; imaging the tissue surface with an array of spatially calibrated digital cameras; choosing camera invariant properties of the fiducial markers and forming camera angle invariant signatures; identifying common markers in the images of a non-actuated tissue between all cameras in the array using the camera angle invariant signatures; tracking the markers on the actuated tissue surface from image to image in each digital camera using a global motion invariant signature; using the tracked motion in each camera and the camera calibration to measure tissue surface motion.

In another form, the invention is a digital image-based elasto-tomography apparatus, comprising: an array of spatially calibrated cameras; a vibration unit situated proximate to the array of cameras; and a computer system in electrical communication with the cameras and configured for computing the surface motion of an object actuated by the vibration unit and within a field of view of the cameras.

The invention has the advantages of accurately and efficiently tracking large numbers of markers that are close together for a large array of digital cameras. The invention has flexibility in varying the type of pattern and shape of the fiducial markers, and distribution density of the fiducial markers for improved accuracy and allows significant freedom in the amount of pixel movement between images in feature registration for improved efficiency.

These and other aspects, objects, features and advantages of the present invention will be more clearly understood and appreciated from a review of the following description of the preferred embodiment and appended claims, and by reference to the accompanying drawings.

BRIEF DESCRIPTION OF THE DRAWINGS

The present invention is disclosed with reference to the accompanying drawings, wherein:

FIG. 3 is a block diagram of a detailed embodiment of the step of determining the motion of the red points as shown in FIG. 2.

Corresponding reference characters indicate corresponding parts throughout the several views. The examples set out herein illustrate several embodiments of the invention but should not be construed as limiting the scope of the invention in any manner.

DETAILED DESCRIPTION

Figure 1A:
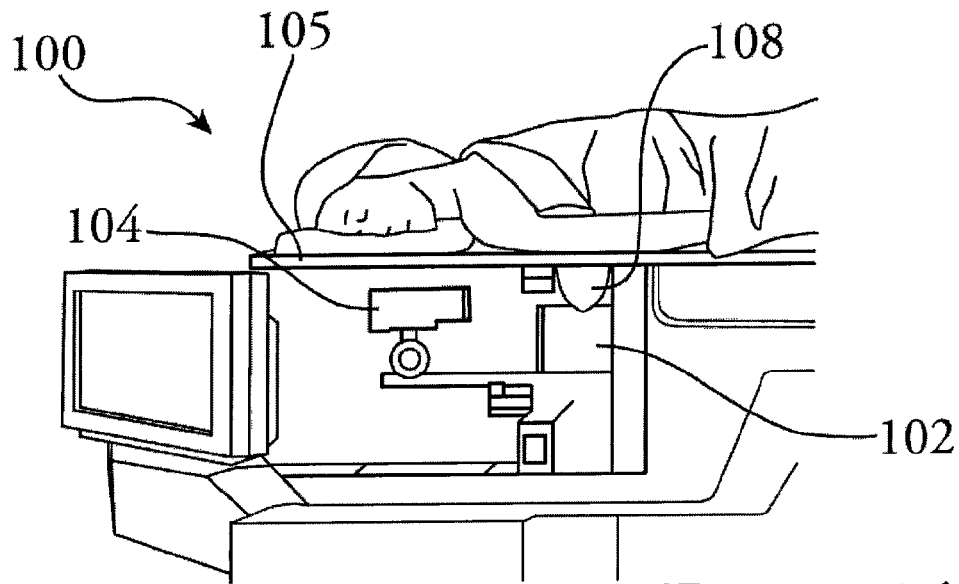
FIG. 1A is a view of an apparatus implementing the DIET system according to the present invention.
Figure 1B:
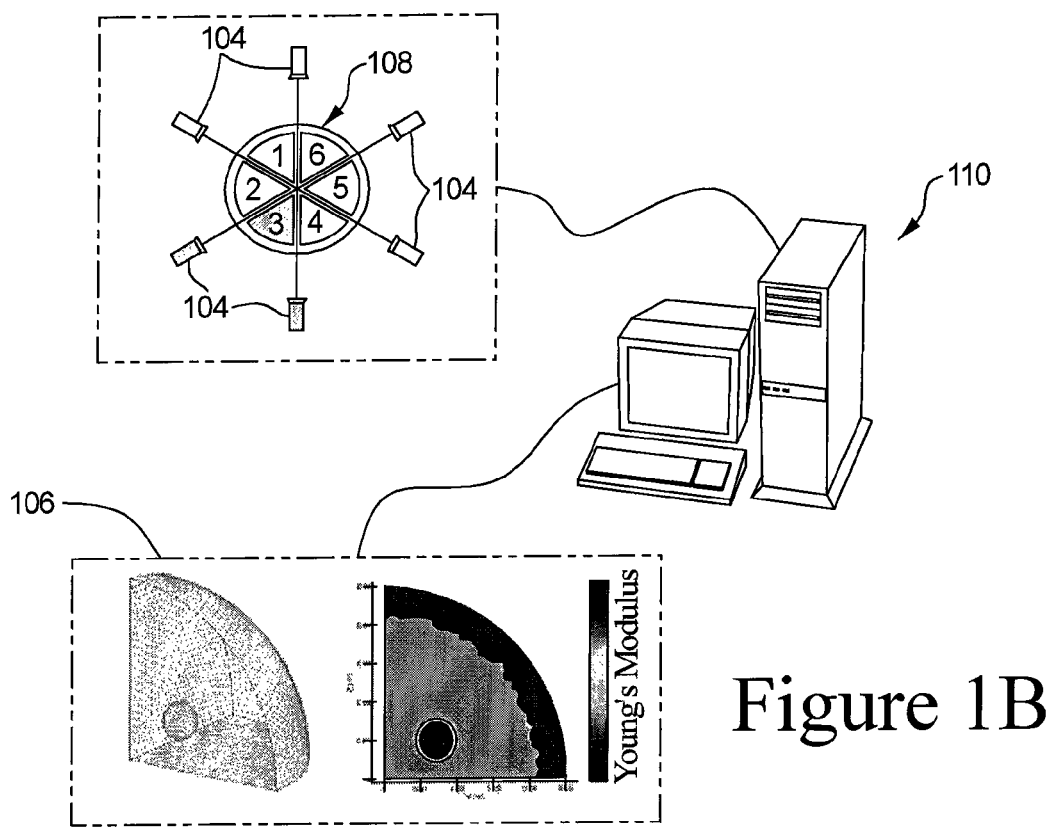
FIG. 1B is a diagram summary of the DIET system.

There are many different methods in the literature for registering images [Jan Modersitzki (2004), "Numerical Methods for Image Registration", Oxford University Press, New York]. These methods are usually either feature or intensity based. Intensity based methods avoid the feature extraction stage but work on whole intensity images so are computationally demanding. In the context of the DIET system as shown in FIGS. 1A and 1B, to capture the full motion of the breast surface with very fine detail requires a large array of high resolution cameras and potentially 1000's of frames for each camera to be analyzed to capture small subtle variations in the breast surface due to a small tumour. Thus methods that work with whole intensity images, for example Normalized Cross-Correlation (NCC) based [J. P. Lewis (1995), "Fast Normalized Cross-Correlation", Vision Interface, 120-123] are not feasible for the DIET system.

Feature based methods are potentially suitable since they minimize the amount of pixel information used. However natural feature extraction on the breast may miss vital areas due to low contrast and consequently miss an abnormal surface perturbation due to a tumour. Thus the DIET system of the present invention preferably relies on tracking high densities of artificially placed fiducial markers. In an alternative embodiment, however, the fiducial markers are features of the tissue itself, such as natural markers or changes in skin tone. This alternative will require higher quality cameras (better contrast) and possibly more image processing, such as the use of color filters, than the preferred embodiment with artificial fiducial markers.

Common methods like snakes [M. Kass, A. Witkin and D. Terzopoiulos (1988), "Snakes: Active Contour Models", International Journal of Computer Vision, 1(4):321-331; N. Peterfreund (1999), "Robust tracking of position and velocity with Kalman Snakes", IEEE Transactions on Pattern Analysis and Machine Intelligence, 21(6):564-569] and gradient decent (GDS) [Q. Qheng and R. Chellapa (1995), Automatic Feature Point Extraction and Tracking in Image Sequences for Arbitrary Camera Motion, International Journal of Computer vision, vol. 15, pp. 31-76] are limited to small numbers of points, track each point separately and are highly dependent on fuzziness or varying light conditions. It only requires one occasion where a particular landmark point jumps to another landmark nearby for the whole trajectory to be corrupted. There are also methods based on surface fitting of the points, for example thin plate splines [H. Chui and A. Rangarajan (2003), "A New Point Matching Algorithm for Non-Rigid Registration", 89 (2-3):114-141]. However the problem with these methods is the significantly large number of points that need to be interpolated over as well as the huge number of times the methods would need to be applied to track tiny to large scale oscillations of the breast surface, especially during non-steady state motion. Thus the DIET system proposes unique challenges for image registration and motion tracking.

The present invention is generally shown in FIGS. 1A and 1B. FIG. 1A shows the apparatus with the patient lying prone on a patient support 105. A vibration unit 102 under the bed/table contacts a breast 108, which is preferably marked with artificial fiducial markers, as described below. In an alternative embodiment, two or more vibration units 102 are used to actuate the breast from different locations. An array of cameras 104 below the bed/table captures images of the breast 108 as it is vibrated by the vibration unit 102. The cameras 104 are preferably high resolution cameras, such as those that produce 1 mega-pixel frames. The vibration unit 102 vibrates the breast 108 at a rate that is close to, but offset from the camera speed. For example, the vibration rate would be about 101 Hz for a camera speed of about 100 frames per second. Of course, the camera speed may be a fraction of 100 frames per second and used with the same vibration rate to achieve similar results. The point is to capture a small amount of movement with each frame. The low vibration rates (on the order of 100 Hz) are chosen (as opposed to ultrasonic rates typically used in elasto-tomography) because the breast tissue is much more responsive to vibrations near those frequencies than higher frequencies, such as ultrasonic frequencies.

As shown in FIG. 1B, the cameras 104 are arrayed around the breast 108 and calibrated such that any point on the breast is visible to at least two cameras. The cameras 104 are spatially calibrated by standard techniques used for tracking points with multiple cameras, and the images captured by the cameras are transmitted to the computer 110 for image registration and motion tracking with software to measure the surface motion of the breast 108. The computer 110 then uses software to convert the surface motion into a stiffness distribution 106.

Accordingly, the present invention focuses on pre-determined qualities and patterns in artificially placed fiducial markers and completely reformulating the problem by computing a global motion invariant signature. According to one aspect of the invention and referring to FIG. 2, markers are randomly applied to the breast according to a class of characteristics with two or more subclasses wherein each subclass has a different number of markers. The class of characteristics may be, for example, color wherein each subclass has markers with a common color that is different from the colors of markers in different classes. For example, one subclass may have red markers and another subclass may have blue markers. In an alternative example, the class is shape and each subclass has markers with a common shape that is different from the shapes of markers in other subclasses. The different shapes may include a triangle, a circle, a square, etc. In another alternative example, the class is size and each subclass has markers with a common size. For simplicity, the invention is described with the markers applied according to a class having three primary colours with subclasses of red, green and blue. In alternative embodiments, the markers may be applied with a local pattern such as pattern having a red marker surrounded by four green markers and sixteen blue markers. Further, the markers may use alternative colors to red, green, and blue.

In step 200 (FIG. 2), the coloured points red, green, and blue are placed with increasing densities in the preferred ratio 1:4:16 where the blue points are in a sufficiently high density to accurately measure surface motion on the scale of $\approx 1$ cm$^2$. Alternative ratios may also be used, such as 1:2:4. The smaller number of red points serve to allow rapid overall motion tracking and the green and blue points account for progressively smaller motions. The invention will accommodate substantially any density of markers; however, generally speaking, the higher the density, the more accurate the results. A user may determine the appropriate density of markers by considering the resolution of the image and the desired accuracy of the analysis. For example, if one wanted an accuracy of 1 mm and a pixel covered a 0.01 mm$^2$ area, a density of less than one marker per pixel would be sufficient. For an accuracy of 1 µm with the same resolution, a density of more than 1-2 dots per pixel would be required.

After identifying blue, green, and red points and a chosen sequence of frames representing breast motion in step 202, the global colour-based signatures representing the red points in each image are computed for each pair of consecutive frames in step 204. This global signature is developed using motion invariant properties of the markers, which do not change substantially between the sequential frames. For example the distances between a particular point and its two closest points is generally motion invariant. Step 204 is shown in more detail in Steps 300 to 308 in FIG. 3 described below. In step 206, the global signature for the red points is used to interpolate between the red points to approximately register first the green and then the blue points from the second frame to the first frame. The system performs a closest point search to match the approximately registered green and blue points to the respective green and blue points of the first frame.

The system then, using the data associated with the spatial calibration of the cameras and cubic splines, computes the 3-D space curves for the red point trajectories parameterized in time for the chosen sequence of frames in step 208. In step 210, the system selects points on the red point 3-D continuous trajectories that correspond to the actual points in the chosen frame sequence to thereby use the computed curves to predict the location of the points in the respective frames. The system computes the error between the predicted and actual motion in step 212 using normalized cross-correlation (NCC) or another error metric. If these computed errors are within tolerances set by the user, step 214 outputs the final surface motion to a data file 216. Otherwise, step 214 returns the system to step 202 to choose a new sequence of frames and repeat the following steps. The loop continues until the error is within tolerances or it is stopped by the user.

These steps are then repeated for each camera to output the surface motion over the entire breast 108. This data may then be used to determine the stiffness distribution 106 throughout the breast, such as with Integral-Based Parameter Identification Applied to three-dimensional Tissue Reconstruction in a DIET System described in my copending patent application Integral-Based Parameter Identification Applied to Three-Dimensional tissue Stiffness Reconstruction in a Digital Image-Based Elasto-Tomography System, application Ser. No. 11/749,633, the disclosure of which is herein incorporated by reference.

Referring to FIG. 3, the system forms the color based global signature of the red points in each of two consecutive frames in the chosen sequence by representing each red point by the distance to the closest green and blue point, respectively, in step 300. Thus the global signature is substantially invariant to local linear or affine transformations. In step 302, the system locates the nearest red point in the second frame to each of the red points in the first frame to provide an initial correspondence of red points in the two frames. The system in step 304 applies a maximum distance between the correlated red points set by a user and eliminates any correlated points that differ by distances higher than this maximum. Step 304 thus eliminates a large number of non-corresponding points.

The system rules out further non-corresponding points in step 306 by forming a triangle between a red point, the closest point to the first red point, and the second closest point to the first red point in the first frame and then comparing the lengths of the three sides to the sides of a triangle formed between the points in the second frame that were correlated to the three points in the first frame in step 302. If the three differences between the three lengths is less than a predetermined tolerance, the two red points are accepted. If any of the differences in lengths are outside the tolerance, both points are rejected as non-corresponding. The remaining red points in the first frame are each correlated to a point in the second frame so the system may compute and output a motion vector between the corresponding dots in step 308. Steps 300-308 are repeated for each set of two consecutive frames in the chosen sequence.

Locally, with a high enough density of points, the motion over a sufficiently small patch on the breast surface will be close to linear. Thus even though some patches will move significantly more than other patches on the breast surface, corresponding to significantly different local linear or affine transformations, the majority of this global difference in motion will be corrected for by the signature. The problem of identifying landmark points between images related by a global motion reduces to the much simpler problem of identifying the overlap of two global motion invariant signatures.

Figure 2:
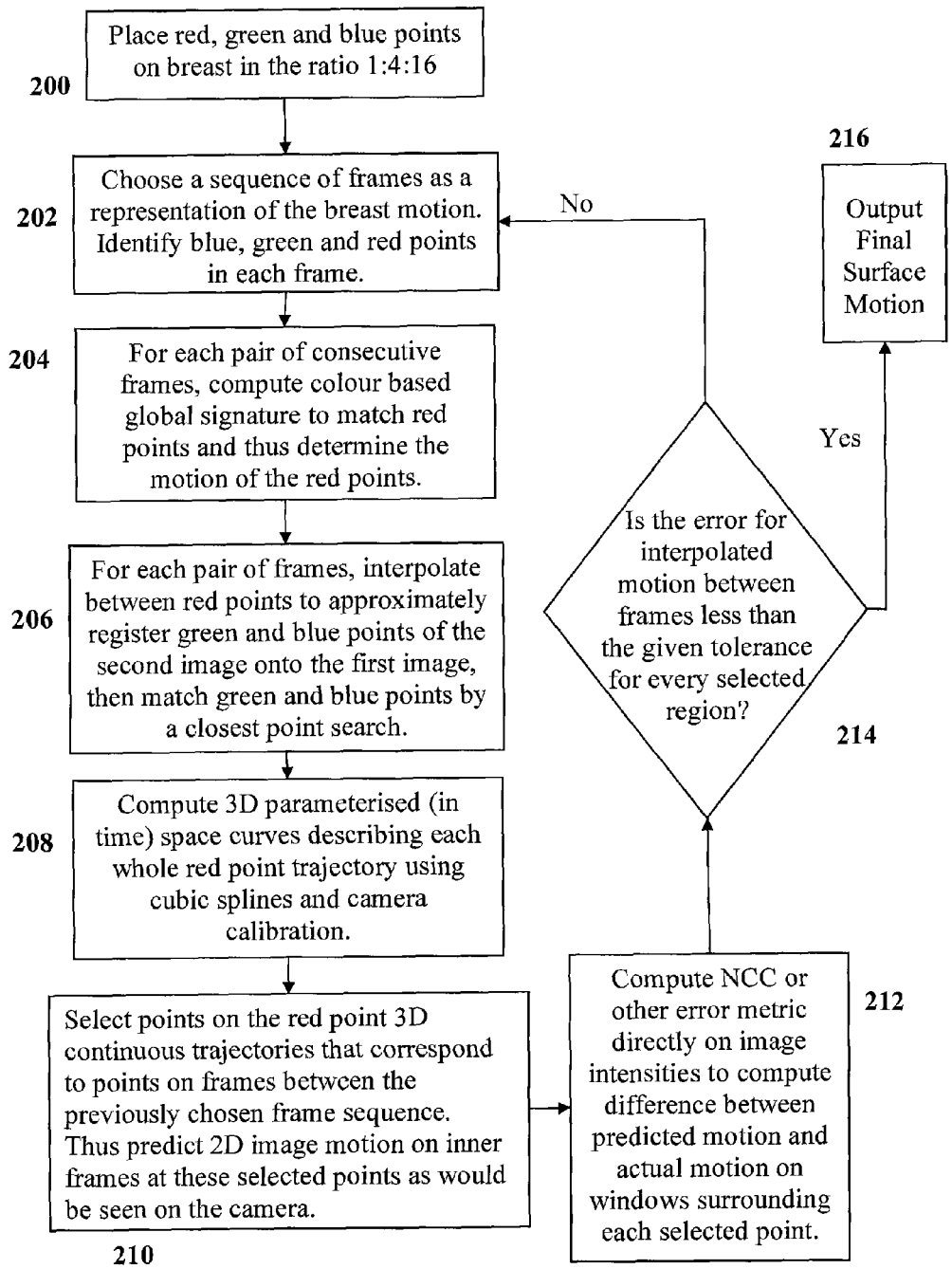
FIG. 2 is a block diagram of a method, according to the present invention, of generating the measurement of the breast surface motion under actuation in a DIET system.

The differing densities of blue, green, and red points serves two purposes. First, they maximise discrimination between non-corresponding landmark points and second, they provide a hierarchical method of matching all the points, dramatically reducing the computation required. Referring to FIG. 2, the hierarchical method involves first matching the smaller density of red points in step 204, then using interpolation and a closest point search to the higher density of green and blue points in step 206.

To specifically demonstrate one aspect of this invention, the rest of this detailed part of the disclosure will consist of three examples which progressively become a more realistic representation of motion tracking in a DIET system. Consider an example where the global motion is a linear transformation:

$$(x,y) \rightarrow (x \cos \theta + y \sin \theta + c, -x \sin \theta + y \cos \theta + f) \quad (1)$$

Figure 4:
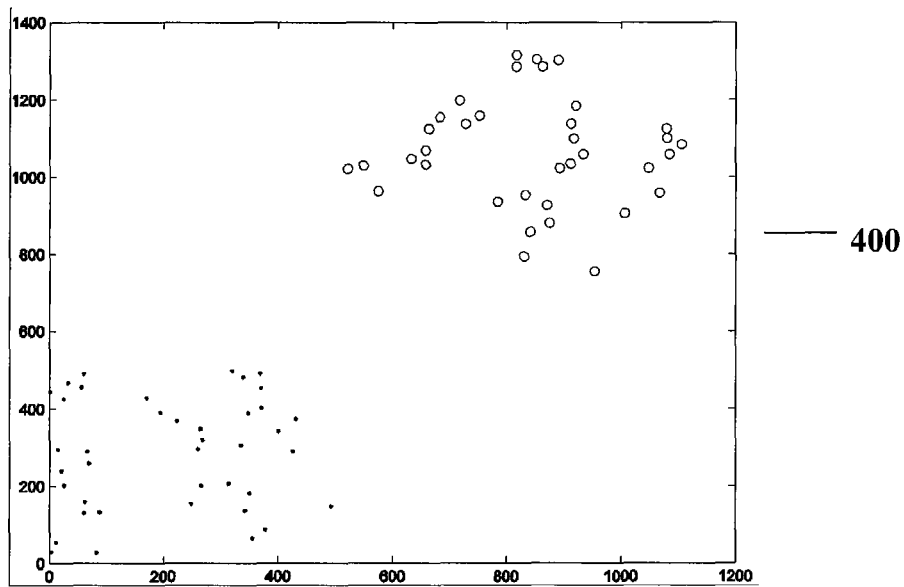
FIG. 4 is an artificially simulated group of blue dots in an image differing by an induced linear motion in a first example.
Figure 5:
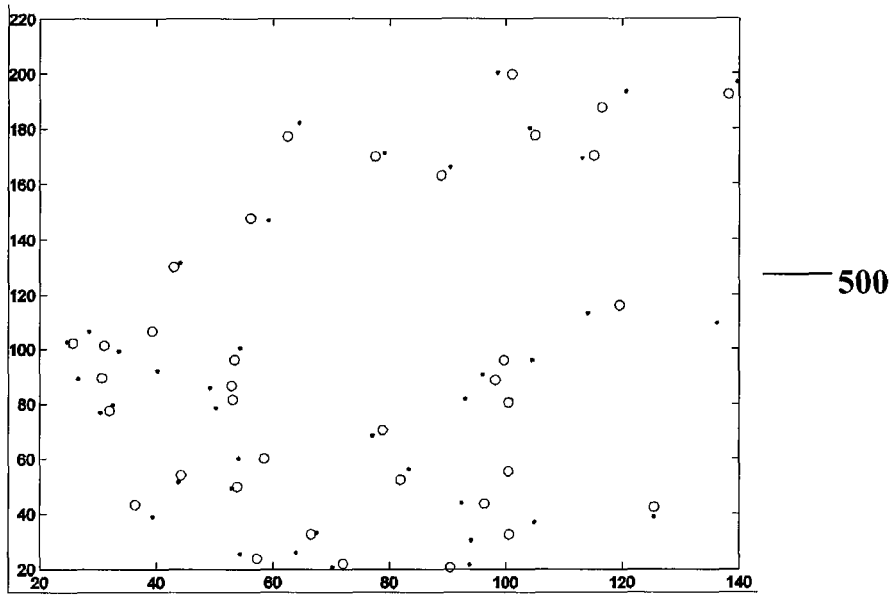
FIG. 5 is the linear invariant signature for the example of blue dots demonstrating the concept in the first example.
Figure 6:
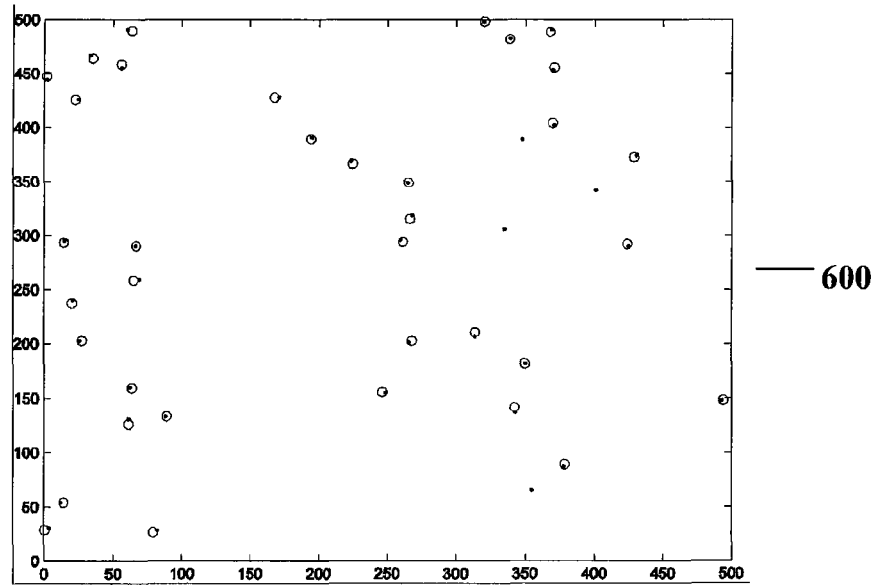
FIG. 6 is the registration of the blue dots between images in the first example.

Let there be 40 blue dots, 20 green, and 10 red dots placed randomly on a 500K pixel image I; though, a ratio of 16:4:1 is preferred in practice. A linear transformation of Equation (1) is applied on image I where $\theta=45°$, $c=500$, $f=1000$ to produce an image $\bar{I}$. Random noise of up to $\pm 3$ pixels is added to the points in I and $\bar{I}$ and 10% of each of the blue, green, and red dots are taken randomly out of the points on $\bar{I}$ to simulate misidentification of colours. The blue dots in the two resulting images are shown in the plot 400 of FIG. 4. In this case the linear invariant signatures are calculated in step 300 for the blue dots and shown in the linear invariant signatures plot 500 of FIG. 5. For this simple proof of concept example, the motion is very large, so steps 302 and 306 are applied without step 304 to match the blue points and rule out non-corresponding points. The resulting corresponding blue points are used to compute the best least squares linear transformation mapping $\bar{I}$ to I. The resulting registration of $\bar{I}$ onto I 600 is shown in FIG. 6. All blue, green, and red points in the registered version of $\bar{I}$ are then matched to the closest blue, green and red points in I within a noise threshold of 6 pixels. This process is repeated for 100 random simulations and no false identifications are made.

Figure 7:
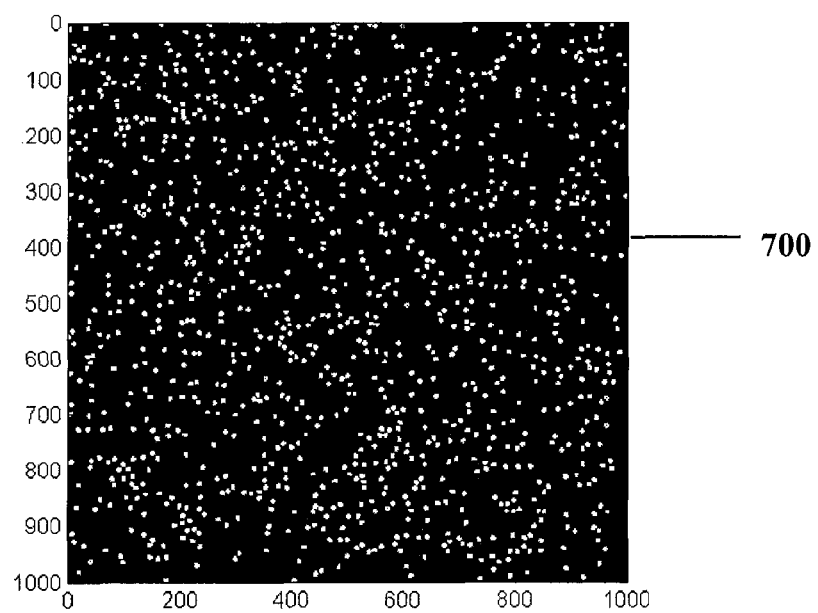
FIG. 7 is an artificially generated binary image containing 1000 circles according to a second example.
Figure 8:
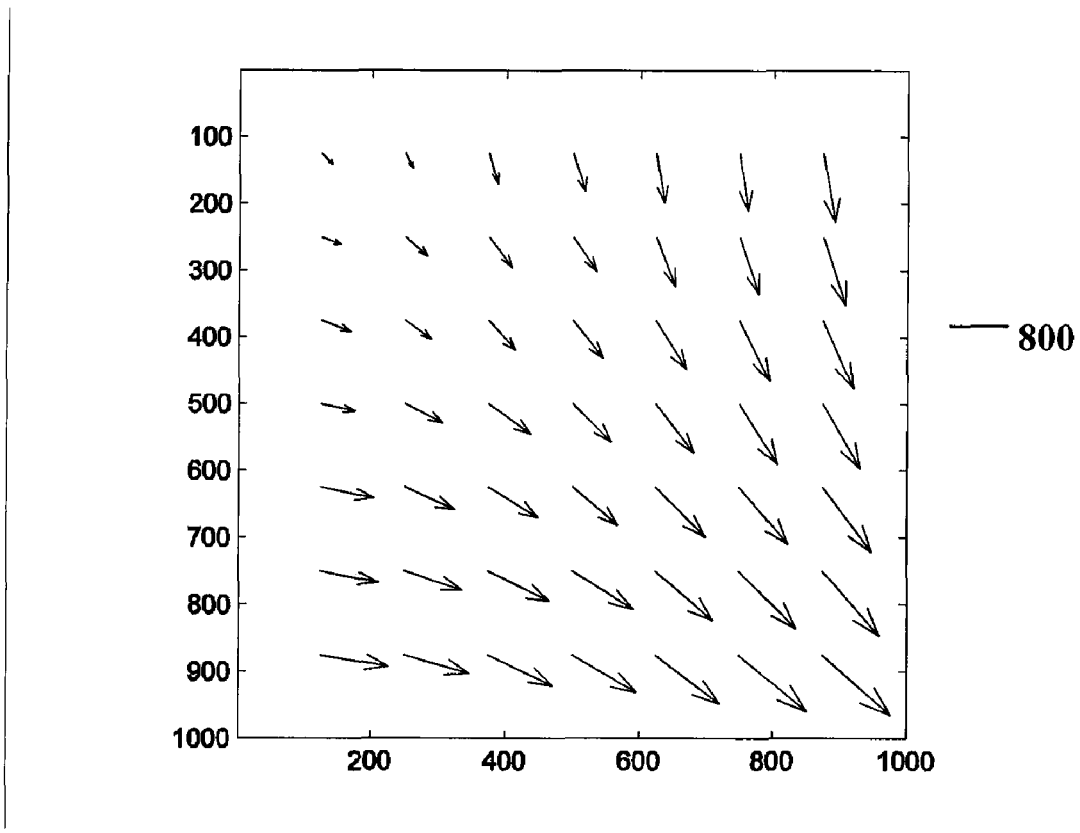
FIG. 8 is the induced motion field of the binary image in FIG. 7.
Figure 9:
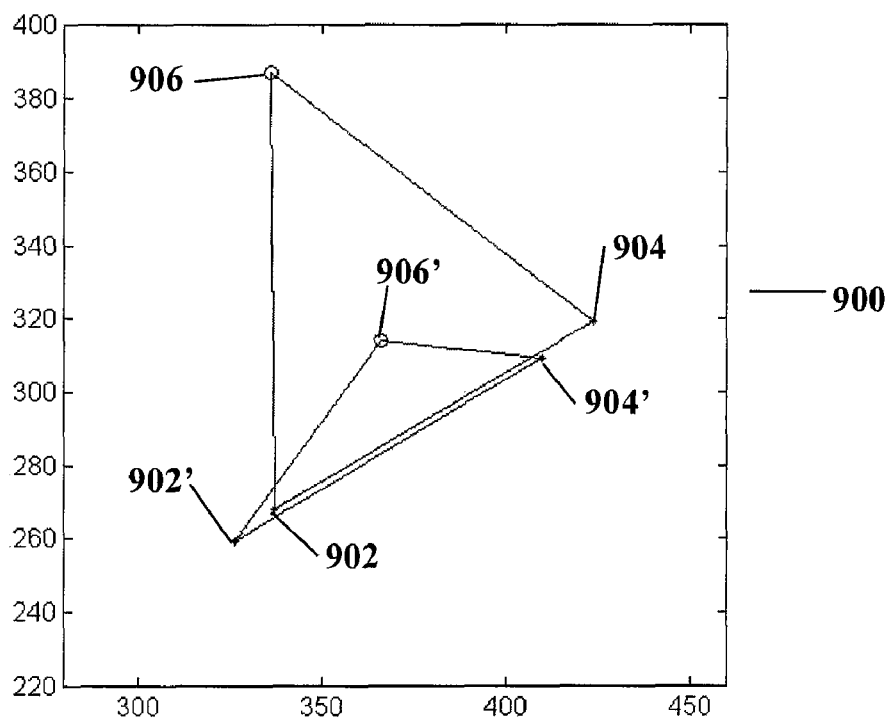
FIG. 9 is a geometric method of ruling out non-corresponding points in the second example.

To demonstrate the concept on a non-uniform global motion field, 1000 circles with a diameter of 10 pixels are randomly placed on a 1 mega-pixel image I shown in the plot 700 of FIG. 7. 144 red points, 285 green points, and 571 blue points are chosen to give a ratio of $\approx 1:2:4$ for the purpose of illustrating the invention, though the preferred ratio is 1:4:16 in practice. The non-uniform motion field 800 shown in FIG. 8 is applied on the image I of FIG. 7 to produce a new image $\bar{I}$. Using the centres of the circles, global signatures for the red points are calculated using step 300, and steps 302-306 are performed to match the red points. FIG. 9 shows a plot 900 illustrating step 306 with three red points, 902, 904, and 906, in I and three red points, 902', 904', and 906', in $\bar{I}$ which are initially corresponding points after step 302 and 304. Point 906/906' is non-corresponding, however, and is denoted by a circle. This demonstrates the importance of Step 306 which would reject the circle of red points since the three distances of the triangle in I are significantly different from the three distances of the corresponding triangle in $\bar{I}$, with a maximum absolute difference of $\approx 67$ pixels, which is much greater than the error tolerance of 10 pixels.

Figure 10:
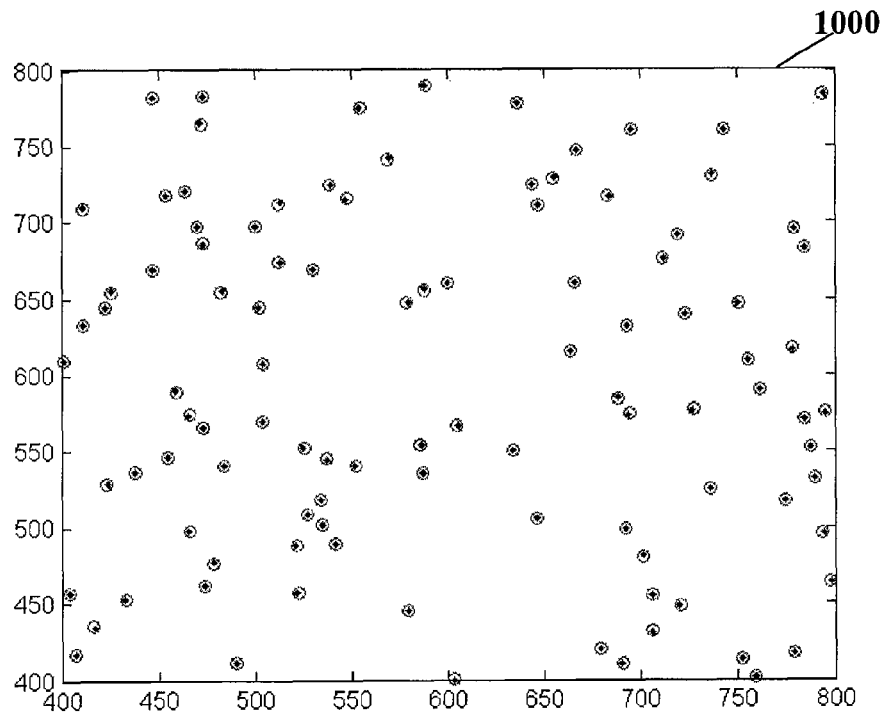
FIG. 10 is the registration of blue points between images in the second example.

Step 206 is then performed where interpolation is done with two-dimensional cubic splines which interpolate x-direction motion and y-direction motion between the red points separately. The plot 1000 of FIG. 10 shows an example of blue points in registered by interpolation between the red points onto blue points of I. After the registration a closest point search matches all red, blue, and green points of image $\bar{I}$ onto I.

Figure 11:
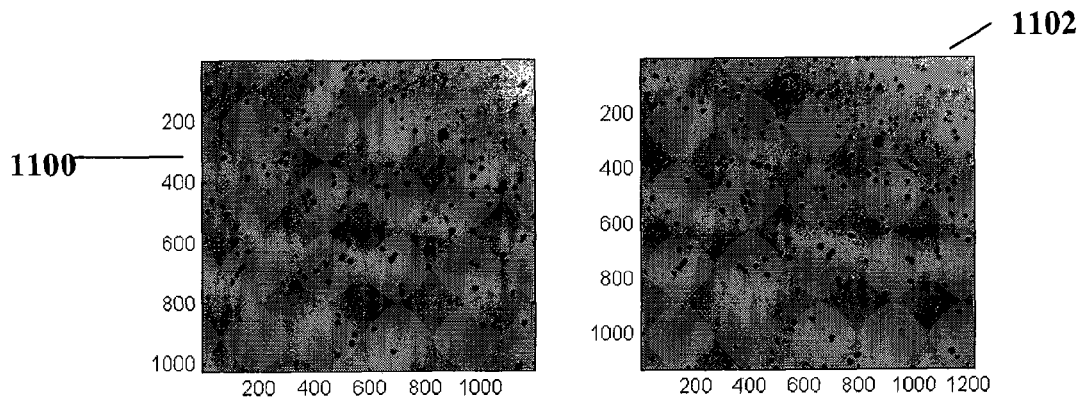
FIG. 11 is two images of deformations of a visco-elastic breast phantom according to a third example.
Figure 12:
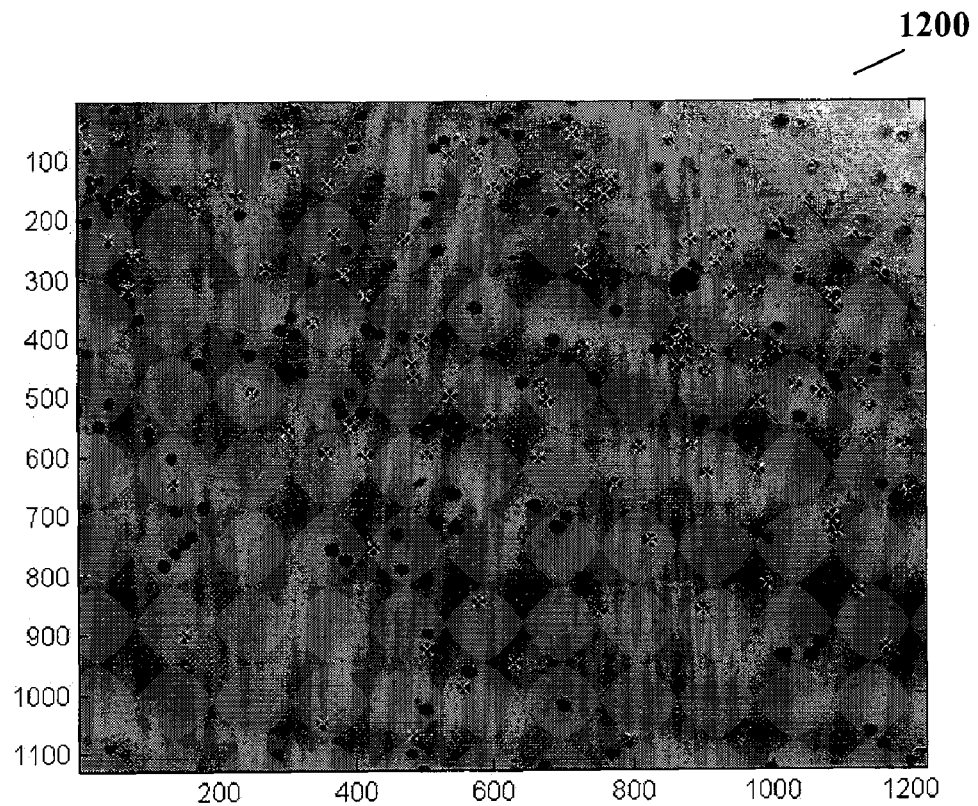
FIG. 12 is the registration of the blue dots between images in the third example.
Figure 13:
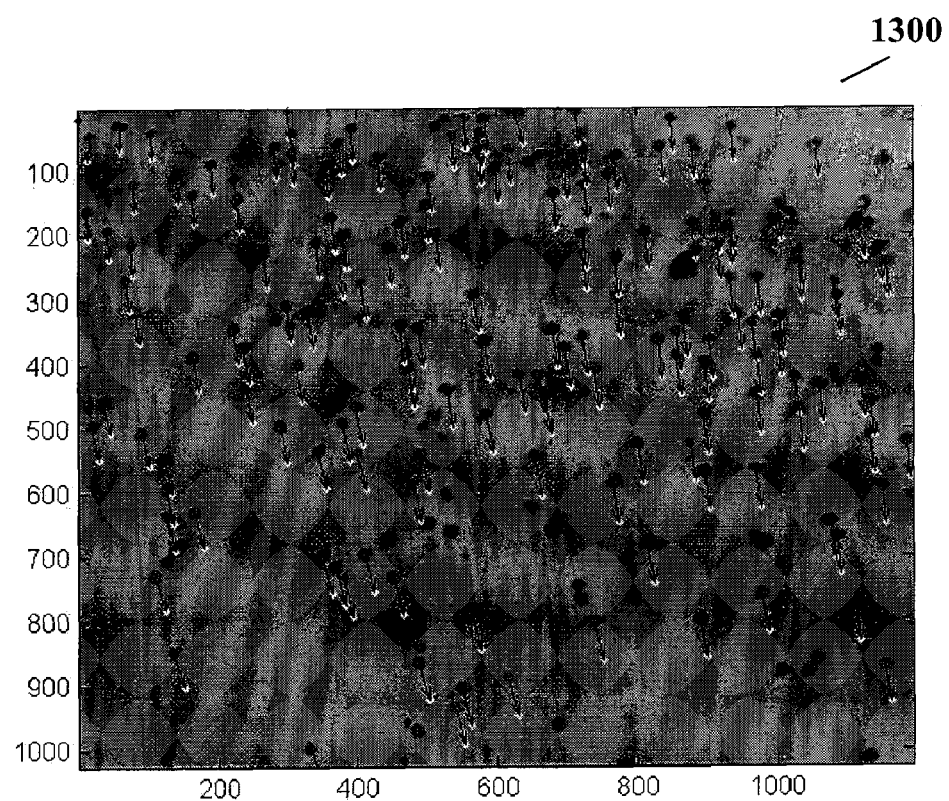
FIG. 13 is the final motion field of all the points in the third example.

Finally, to prove the concept on real images, two $\approx 1$ mega-pixel images 1100 and 1102 of two different deformations of a visco-elastic breast phantom with randomly placed coloured markers were taken, as shown in FIG. 11 though the colors are not shown in the black and white figures. Using a combination of thresholding and labeling connected 1 pixel paths, the centre and colour of each marker are found. For simplicity, markers that overlap are automatically detected and are not used to build the signature. Applying steps 302-306 to determine the motion of the red points 204, then interpolating the red points using two-dimensional cubic splines, to approximately register the green and blue points produces the registered images 1200 shown for the blue points in FIG. 12. The blue points corresponding to the image 1102 in FIG. 11 are denoted by crosses in FIG. 12 and show a close match. A closest point search is then performed to match the crosses precisely to the corresponding points in the image 1100 in FIG. 11, which produces the motion field 1300 shown in FIG. 13 for all the red, green, and blue points excluding overlaps.

The signature method can be applied on all consecutive pairs of frames in an actuation sequence to track a high density of points very accurately and with minimal computation. Furthermore the method is not restricted to very small motion between images and so the method of adaptive frame sampling in steps 202-214 can be applied, significantly further reducing computation. Thus a global colour-based motion invariant signature utilizing different proportions of fiducial markers in a hierarchical structure is a very effective method for tracking large numbers of points, ensuring that small local perturbations as well as large global motions on the breast surface can be accurately measured with low computational requirements.

In an alternative embodiment, the markers may be applied in a global pattern, such as in the case that the markers are applied to the breast with a template. In a further alternative embodiment, the colors of the markers may be ignored, or the markers may be applied in a single color.

The patient support 105 shown in FIG. 1A is illustrated as a bed/table with the patient in a prone position; however the DIET system 100 may be alternatively configured with the patient in a supine position. Further, the patient support 105 may be configured as a platform or a seat with the patient in a non-horizontal position.

The invention has been described as tracking the surface motion of a breast for the purpose of providing data that may be used to determine the stiffness distribution throughout the breast. However, the invention may alternatively be used to track the surface motion of any organ or tissue wherein dysfunction or damage may be determined by altered or variable tissue elastic, damping, or mass properties. Further the invention may be used in conjunction with MRI, laser sheets, point laser, PIV methods via digital or analog imaging, or ultrasound.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Parts List
100 DIET System
102 vibration unit
104 arrayed and calibrated digital cameras
105 patient support
106 stiffness distribution of breast
108 breast
110 computer
200 step of placing points on breast
202 step of choosing sequence of frames and identifying points
204 step of determining the global motion invariant signature to track red points
206 step of interpolation to register blue and green points
208 step of computing three-dimensional trajectories
210 step of predicting motion between frames
212 step of comparing predicted motion with actual motion
214 step of determining if the results are within chosen tolerances
216 step of outputting the surface motion
300 step of computing global signature using closest distances
302 step of determining the initial correspondence of red points
304 step of performing the first test for ruling out points
306 step of performing the second test for ruling out points
308 step of outputting the corresponding red points
400 first example plot showing blue dots in images I and Ī
500 linear invariant signatures plot
600 registration of blue dots in Ī onto I
700 second example—binary image plot
800 motion field
900 plot illustrating step 306
902, 904, and 906 red points in I
902', 904', and 906' red points in Ī
1000 plot registering blue dots
1100 third example—visco-elastic breast phantom image—first deformation
1102 visco-elastic breast phantom image—second deformation
1200 registered image
1300 motion field

The invention claimed is:

1. A method of tracking fiducial markers on a surface of images of body tissue with a digital image-based elastotomography system, said method comprising the steps of:
   placing a plurality of fiducial markers on a tissue surface;
   actuating the tissue surface to move the tissue and the fiducial markers on the tissue surface;
   imaging the tissue surface with an array of calibrated digital cameras;
   choosing motion invariant properties of the fiducial markers to form a global motion invariant signature:
   wherein there are a plurality of subclasses of fiducial markers on the tissue surface and each subclass comprises markers with a unique characteristic different from unique characteristics of other fiducial markers of other subclasses;
   tracking the fiducial markers on the actuated tissue surface from image to image in each calibrated digital camera using the global motion invariant signature; and
   using the motion of each fiducial marker as tracked from image to image in each calibrated camera and each camera's calibration to measure tissue surface motion.

2. The method of claim 1 wherein the unique characteristic of each marker is the colour of the marker.

3. The method of claim 2 wherein each subclass has fiducial markers in a unique colour selected from the group consisting essentially of red, green, blue and black.

4. The method of claim 2 wherein the fiducial markers are applied in glitter paint.

5. The method of claim 1 wherein the unique characteristic of each marker is the shape of the marker.

6. The method of claim 1 wherein one motion invariant property is a distance between a fiducial marker of one subclass and a closest fiducial marker of another subclass.

7. The method of claim 1 wherein a motion invariant property is, within a predefined neighborhood, a total number of unique fiducial markers in one subclass in said neighborhood compared to a total number of other unique fiducial markers of other subclasses in said neighborhood.

8. The method of claim 7 further comprising the step of determining three-dimensional coordinates of the fiducial markers according to a spatial calibration of the cameras, wherein the predefined neighborhood is all markers within a chosen distance of each marker in a particular class as measured using the three-dimensional coordinates.

9. The method of claim 7 wherein the motion invariant properties of one subclass of fiducial markers comprise distances between a fiducial marker in the one subclass closest to fiducial markers in other subclasses.

10. The method of claim 7 wherein the subclass of fiducial markers that are in the smallest proportion are used to form the global motion invariant signature.

11. The method of claim 1 wherein the markers are randomly distributed on the body tissue.

12. The method of claim 1 wherein the body tissue is a breast.

13. The method of claim 1 further comprising:
   capturing sequential images of fiducial marks while the body tissue is moving; and
   registering the captured images with one another to establish distances the fiducials travel while the body tissue is moving.

14. A method of tracking fiducial markers on a surface of images of body tissue with a digital image-based elastotomography system said method comprising the steps of:
   placing a plurality of fiducial markers on a tissue surface;
   imaging the tissue surface with an array of spatially calibrated digital cameras;
   choosing camera invariant properties of the fiducial markers and forming camera angle invariant signatures;
   identifying common markers in images of a tissue surface between all cameras in the array using the camera angle invariant signatures;
   actuating the tissue surface to move the tissue and the fiducial markers on the tissue;
   tracking the motion of the fiducial markers on the actuated tissue surface from image to image in each digital camera using a global motion invariant signature;

using the motion of each marker as tracked from image to image in each calibrated camera to measure tissue surface motion.

15. The method of claim 14 wherein the camera angle invariant properties are affine invariant or projective invariant.

16. The method of claim 15 further comprising the steps of classifying the fiducial markers according to a chosen characteristic and grouping markings having common characteristics into subclasses; choosing one of the subclasses; determining the two or more closest points in non-chosen subclasses to each marker in the chosen subclass; and forming affine and projective invariant ratios of triangular areas between the markers.

17. The method of claim 16 wherein the characteristics are selected from the group consisting essentially of colours and shapes.

18. The method as claimed in claim 16 wherein the chosen characteristic is color and the fiducial markers comprise glitter paint in colours selected from the group consisting essentially of red, blue, green and black.

19. The method of claim 14 wherein the markers are randomly distributed on the body tissue.

20. The method of claim 14 wherein the body tissue is a breast.

21. The method of claim 14 further comprising:
capturing sequential images of fiducial marks while the body tissue is moving; and
registering the captured images with one another to establish distances the fiducials travel while the body tissue is moving.

* * * * *